US007723320B2

(12) United States Patent
Bunschoten et al.

(10) Patent No.: US 7,723,320 B2
(45) Date of Patent: May 25, 2010

(54) USE OF ESTROGEN COMPOUNDS TO INCREASE LIBIDO IN WOMEN

(75) Inventors: Evert Johannes Bunschoten, Heesch (NL); Herman Jan Tijmen Coelingh Bennink, Driebergen (NL); Christian Franz Holinka, New York, NY (US)

(73) Assignee: Pantarhei Bioscience B.V., Al Zeist (NL)

( * ) Notice: Subject to any disclaimer, the term of this patent is extended or adjusted under 35 U.S.C. 154(b) by 1072 days.

(21) Appl. No.: 10/478,264

(22) PCT Filed: May 17, 2002

(86) PCT No.: PCT/NL02/00316

§ 371 (c)(1),
(2), (4) Date: May 25, 2004

(87) PCT Pub. No.: WO02/094275

PCT Pub. Date: Nov. 28, 2002

(65) Prior Publication Data

US 2004/0186086 A1    Sep. 23, 2004

(30) Foreign Application Priority Data

May 18, 2001   (EP)   ................... 01201896

(51) Int. Cl.
*A61K 31/56* (2006.01)
(52) U.S. Cl. ...................... 514/171; 514/182
(58) Field of Classification Search ............. 514/171
See application file for complete search history.

(56) References Cited

U.S. PATENT DOCUMENTS 5,340,584 A * 8/1994 Spicer et al. ............... 424/426
5,340,586 A   8/1994 Pike et al.
5,468,736 A   11/1995 Hodgen

FOREIGN PATENT DOCUMENTS

DE   23 36 433 A   4/1975
DE   23 36 434 A   4/1975
WO   WO 96 03929 A   2/1996

OTHER PUBLICATIONS

Holinka C F et al; "Comparison of Effects of Estetrol and Taxoxifen with Those of Estriol and Estradiol on the Immature Rat Uterus"; Biology of Reproduction; 1980; pp. 913-926; vol. 22, No. 4.
Holinka C F et al; "In-Vivo Effects of Estetrol on the Immature Rat Uterus"; Biology of Reproduction; 1979; pp. 242-246; vol. 20, No. 2.
Albertazzi Paola et al; "The Effect of Tibolone Versus Continuous Combined Norethisterone Acetate and Oestradiol on Memory, Libido and Mood of Postmenopausal Women: A pilot study"; Database Biosis 'Online!; Oct. 31, 2000; pp. 223-229; vol. 36, No. 3; Biosciences Information Service,; Philadelphia, PA, US.
Visser et al., "In vitro effects of estetrol on receptor binding, drug targets and human liver cell metabolism," Climacteric (2008) 11(1) Appx. II: 1-5.
Visser et al., "First human exposure to exogenous single-dose oral estetrol in early postmenopausal women," Climacteric (2008) 11(1): 1-10.
Visser et al., "Clinical applications of estetrol," J. Of Steroid Biochem and Molecular Biol. (2009) 114: 85-89.
Holinka et al., "Estetrol: A unique steroid in human pregnancy," J. of Steroid Biochem and Molecular Biol. (2009) 110: 138-143.
Coelingh Bennink et al., "Oral bioavailability and bone sparing effects of estetrol in an osteoporosis model," Climacteric (2008) 11 (Supp 3): 1-13.

* cited by examiner

*Primary Examiner*—San-ming Hui
(74) *Attorney, Agent, or Firm*—The Webb Law Firm

(57) ABSTRACT

Disclosed is a method of increasing libido in a woman, said method comprising administering to said woman an effective amount of an estrogenic component selected from the group consisting of: substances represented by the following formula (I) in which formula $R_1$, $R_2$, $R_3$, $R_4$ independently are a hydrogen atom, a hydroxyl group or an alkoxy group with 1-5 carbon atoms; each of $R_5$, $R_6$, $R_7$ is a hydroxyl group; no more than 3 of $R_1$, $R_2$, $R_3$, $R_4$ are hydrogen atoms; precursors capable of liberating a substance according to the aforementioned formula when used in the present method; and mixtures of one or more of the aforementioned substances and/or precursors.

12 Claims, No Drawings

USE OF ESTROGEN COMPOUNDS TO INCREASE LIBIDO IN WOMEN

TECHNICAL FIELD OF THE INVENTION

The present invention relates to a method of increasing libido in a woman, said method comprising administering an effective amount of an estrogenic component to said woman

BACKGROUND OF THE INVENTION

The presence of a normal libido, defined as the urge to engage in sexual activity and intercourse, is an important component of an individual's well-being. Low or decreased libido is a common complaint in women. Such complaints are observed in pre peri- as well as post-menopausal women.

A low libido is characterised by a lack of interest in sexual intercourse and/or the lack of ability to achieve orgasm. A decreased libido may be accompanied by a decrease in intensity of orgasm. It is important to note that a decrease in libido is often associated with a profound sense of loss of a once normal and active interest in sexual activity.

U.S. Pat. No. 6,284,263 (Place) is concerned with a method of treating sexual dysfunction in female individuals, comprising bucally administering a therapeutically effective amount of an androgenic agent, a progestin and an estrogen. The US-patent specifically mentions the following estrogens: 17α-estradiol, 17β-estradiol, ethinyl estradiol, pharmaceutically acceptable esters and ethers of 17α-estradiol, 17β-estradiol and ethinyl estradiol, estriol, estriol succinate, polyestrol phosphate, estrone, estrone acetate, estrone sulfate, piperazine estrone sulfate, quinestrol, mestranol and conjugated equine estrogens. As explained in the US-patent, vaginal atrophy and dyspareunia are a common cause of sexual dysfunction.

In an article by Grio et al., Minerva Ginecol, "Sexuality in menopause. Importance of adequate replacement therapy" (1999), 51(3), 59-62, it is observed that estrogen deficiency in menopause is responsible for reduced libido and uncomfortable trophic disorders of the urogenital tract leading to reduced vaginal lubrication and severe alterations affecting sexual function. The authors treated 102 menopausal patients who presented reduced libido and orgasmic difficulties, as well as other menopausal problems, with 17-β estradiol and norethisterone acetate using a transdermal route. It is noted in the article that the main advantage offered by the transdermal route is that estrogens bypass the liver and reach the target organs in an unmodified manner. The authors conclude that the use of 17-β estradiol and norethisterone acetate can effectively modify menopausal symptoms, improving both quality of life and sexual function.

Well-known estrogens, in particular biogenic estrogens (i.e. estrogens that occur naturally in the human body), are eliminated from the blood stream very quickly. For instance, for the main human biogenic estrogen 17β-estradiol the half-life is around 1 hour. As a result, between separate administration events, blood serum levels of such biogenic estrogens tend to fluctuate considerably. Thus, shortly after administration, the serum concentration is usually several times higher than the optimum concentration. In addition, if the next administration event is delayed, serum concentrations will quickly decrease to a level where the estrogen is no longer physiologically active.

The most important synthetically altered estrogenic steroid is 17α-ethinyl estradiol (EE). This estrogen is dominant in oral hormonal contraception. Apart from EE, mestranol has been used in a few cases; mestranol is a "prodrug" that is metabolised to EE in the organism. The liver is a target organ for estrogens. The secretion activity that is affected by estrogens in the human liver includes increased synthesis of transport proteins CBG, SHBG, TBG, several factors that are important for the physiology of blood clotting, and lipoproteins. The strong hepatic estrogenicity of ethinyl estradiol and diethylstilbestrol (DES), especially their effect on haemostasis factors, may explain why these synthetic estrogens have been associated with the enhanced risk of thromboembolism. Other undesirable side-effects that have been reported in relation to the use of synthetic estrogens include, fluid retention, nausea, bloating, chlolelithiasis, headache, breast pain and an enhanced risk of breast cancer with longer term usage.

The aforementioned deficits are of considerable clinical significance when commonly known biogenic or synthetic estrogens are applied. Consequently, there is an as yet unmet need for estrogens that do not display these deficits and which can suitably be employed in a method of increasing libido in women.

SUMMARY OF THE INTENTION

The inventors have unexpectedly found that a special group of estrogenic substances do not exhibit the aforementioned drawbacks and can be used very effectively to improve libido in women. These estrogenic substances are represented by the following formula

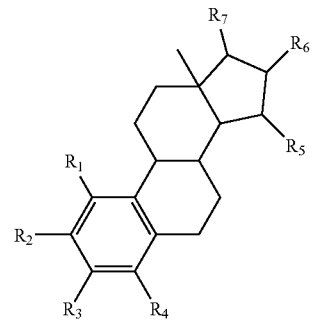

in which formula $R_1$, $R_2$, $R_3$, $R_4$ independently are a hydrogen atom, a hydroxyl group or an alkoxy group with 1-5 carbon atoms; each of $R_5$, $R_6$, $R_7$ is a hydroxyl group; no more than 3 of $R_1$, $R_2$, $R_3$, $R_4$ are hydrogen atoms.

These estrogens are different from the estrogens commonly applied in estrogen replacement therapy, i.e. ethinyl estradiol, estradiol and its esters such as the acetate, valerate or benzoate, mestranol, the conjugated equine estrogens and estrone sulfate.

A known representative of this group of estrogenic substances is 1,3,5(10)-estratrien-3, 15α,16α,17β-tetrol, also known by the names of estetrol, oestetrol and 15α-hydroxyestriol. Estetrol is an estrogen that is produced by the fetal liver during human pregnancy. Unconjugated estetrol levels in maternal plasma peak at about 1.2 ng/ml at term pregnancy and are about 12 times higher in fetal than in maternal plasma (Tulchinsky et al., 1975. J. Clin. Endocrinol. Metab., 40, 560-567).

In 1970, Fishman et al., "Fate of 15α-hydroxyestriol-³H in Adult Man", J Clin Endocrinol Metab (1970) 31, 436-438, reported the results of a study wherein tritium labeled 15α-hydroxyestriol (estetrol) was administered intravenously to two adult women. It was found that the estetrol was rapidly and completely excreted in urine as the glucosiduronate and that virtually no metabolism except for conjugation took place.

Between 1975 and 1985 several researchers have investigated the properties of estetrol and reported on its estrogenic potency and uterotrophic activity. The most relevant publications that were issued during this period are mentioned below:

Levine et al., 1984. Uterine vascular effects of estetrol in nonpregnant ewes. Am. J. Obstet. Gynecol. 148:73, 735-738: "When intravenously administered in nonpregnant ewes, estetrol is 15 to 30 times less potent than estriol and 17β-estradiol in uterine vasodilation".

Jozan et al., 1981. Different effects of oestradiol, oestriol, oestetrol and of oestrone on human breast cancer cells (MCF-7) in long term tissue culture. Acta Endocrinologica, 98, 73-80: "Estetrol agonistic potency is 2% of the magnitude observed for 17β-estradiol in in vitro cell proliferation".

Holinka et al., 1980. Comparison of effects of estetrol and tamoxifen with those of estriol and estradiol on the immature rat uterus. Biol. Reprod. 22, 913-926: "Subcutaneously administered estetrol has very weak uterotrophic activity and is considerable less potent than 17β-estradiol and estriol".

Holinka et al., 1979. In vivo effects of estetrol on the immature rat uterus. Biol. Reprod. 20, 242-246: "Subcutaneously administered estetrol has very weak uterotrophic activity and is considerable less potent than 17β-estradiol and estriol".

Tseng et al., 1978. Heterogeneity of saturable estradiol binding sites in nuclei of human endometrium. Estetrol studies. J. Steroid Biochem. 9, 1145-1148: "Relative binding of estetrol to estrogen receptors in the human endometrium is 1.5% of 17β-estradiol".

Martucci et al., 1977. Direction of estradiol metabolism as a control of its hormonal action-uterotrophic activity of estradiol metabolites. Endocrin. 101, 1709-1715: "Continuous administration of estetrol from a subcutaneous depot shows very weak uterotrophic activity and is considerably less potent than 17β-estradiol and estriol".

Tseng et al., 1976. Competition of estetrol and ethynylestradiol with estradiol for nuclear binding in human endometrium. J. Steroid Biochem. 7, 817-822: "The relative binding constant of estetrol binding to the estrogen receptor in the human endometrium is 6.25% compared to 17β-estradiol (100%)".

Martucci et al., 1976. Uterine estrogen receptor binding of catecholestrogens and of estetrol (1,3,5(10)-estratriene-3,15alpha,16alpha, 17beta-tetrol). Steroids, 27, 325-333: "Relative binding affinity of estetrol to rat uterine cytosol estrogen receptor is 0.5% of 17β-estradiol (100%). Furthermore, the relative binding affinity of estetrol to rat uterine nuclear estrogen receptor is 0.3% of 17β-estradiol (100%)".

All of the above publications have in common that the authors have investigated the estrogenic potency of estetrol. Without exception they all conclude that estetrol is a weak estrogen. In some of the cited articles the estrogenic potency of estetrol has been found to be lower than that of another biogenic estrogen, namely, 17β-estradiol, which is considered to be a relatively weak estrogen (e.g. compared to ethinyl estradiol). With these findings in mind, it is not surprising that the interest in estetrol has dwindled since the early eighties and that no publications on the properties of estetrol have been issued since.

U.S. Pat. No. 5,468,736 (Hodgen) describes a method of hormone replacement therapy involving the administration of estrogen together with an amount of antiprogestin (antiprogestogen), which inhibits estrogen-induced endometrial proliferation in women. In Example 3 the combined use of estetrol and lilopristone is mentioned. No clues are given in the examples as to the mode and frequency of administration or regarding the dosage level employed. A disadvantage associated with the use of antiprogestogens, such as lilopristone, is the risk of inducing abnormal endometrial morphology, i.e. cystic hyperplasia, as has been observed in women who received an antiprogestogen treatment against endometriosis (Murphy et al., 1995. Fertil. Steril., 95, 761-766). Furthermore it is noted that antiprogestogens are a well-known abortive agent and consequently should not be used by women at a fertile age who wish to conceive. The benefits of the present invention may be realised without the application of an antiprogestogen.

In view of the low estrogenic potency of the estetrol-like substances that are employed in accordance with the invention, it is surprising that these substances can effectively be used in the present method. Although the inventors do not wish to be bound by theory, it is believed that the unexpected efficacy of enterally or parenterally administered estetrol-like substances results from the combination of unforeseen favourable pharmacokinetic (ADME) and pharmacodynamic properties of these substances.

As regards the pharmacokinetic properties of the present estrogenic substances the inventors have discovered that their in vivo half-life is considerably longer than that of other. biogenic estrogens. Thus, even though estetrol and estetrol-like substances have relatively low estrogenic potency, they may effectively be employed in the present method because their low potency is compensated for by a relatively high metabolic stability, as demonstrated by a long half-life.

In addition, it is believed that the unexpected efficacy of the present estetrol-like substances may be explained by the relatively high affinity for the estrogen receptor α (ERα) as compared to the estrogen receptor β (ERβ). The latter characteristic is an unique feature of the estrogenic substances employed in the present method. The relatively high affinity of the present estrogenic substances for the ERα receptor, or conversely the relatively low affinity for the ERβ receptor, is believed to be somehow associated with the high efficacy of the present substances as libido enhancers.

Recent publications strongly suggest that the ERα gene expression plays a key role in sexual behaviour of mammals. Ogawa et al., "Roles of Estrogen Receptor-α Gene Expression in Reproduction-Related Behaviors in Female Mice", Endocrinology (1998), 139, 5070-81 report the results of studies into the sexual behavior of estrogen receptor knockout (ERKO) mice. It was found that gonadectomised female ERKO mice that were deficient specifically for the ERα, but not for the ERβ, gene, did not show any lordosis response to the treatment with estrogen or estrogen plus progesterone.

Another study by the same authors (Ogawa et al., "Survival of reproductive behaviors in estrogen receptor β gene-deficient (βERKO) male and female mice", Neurobiology (1999), 96, 12887-92, was conducted in estrogen receptor β gene-deficient (βERKO) male and female mice. It was found that females lacking a functional β isoform of the ER gene showed normal lordosis and courtship behaviors. According to the authors these results highlight the importance of ERα for the normal expression of natural reproductive behaviors.

In summary, although the mechanisms by which the present estrogenic substances exert their favourable effect are not fully understood, it is evident that these substances differ from other biogenic estrogens in 2 important aspects. Firstly the present estrogenic substances exhibit a surprisingly long in vivo half-life. Secondly the ratio between the affinity of these substances for the ERα and the ERβ receptor is much higher than that of other known (biogenic) estrogens.

Another advantageous property of the present estrogenic substances resides in the fact that sex hormone-binding globulin (SHBG) hardly binds these estrogenic substances, meaning that, in contrast to most known estrogens, serum levels are representative for bio-activity and independent of SHBG levels. In addition, this means that the impact of an administered dosage, particularly in case such an administration constitutes an isolated event, is not suppressed as a result of inactivation by SHBG-binding.

A further benefit of the present estrogenic substances is derived from their relative insensitivity to interactions with other drugs (drug-drug interactions). It is well known that certain drugs may decrease the effectiveness of estrogens, such as ethinyl estradiol, and other drugs may enhance their activity, resulting in possibly increased side-effects. Similarly estrogens may interfere with the metabolism of other drugs. In general, the effect of other drugs on estrogens is due to interference with the absorption, metabolism or excretion of these estrogens, whereas the effect of estrogens on other drugs is due to competition for metabolic pathways.

The clinically most significant group of estrogen-drug interactions occurs with drugs that may induce hepatic microsomal enzymes which may decrease estrogen plasma levels below therapeutic level (for example, anticonvulsant agents; phenytoin, primidone, barbiturates, carbamazepine, ethosuximide, and methosuximide; antituberculous drugs such as rifampin; antifungal drugs such as griseofulvin). The present estrogenic substances are less dependent on up- and downregulation of microsomal liver enzymes (e.g. P450's) and also are less sensitive to competition with other P450 substrates. Similarly, they do not interfere significantly in the metabolism of other drugs.

The conjugates of most estrogens, as formed in the liver, are excreted in the bile and may be broken down by gut bacteria in the colon to liberate the active hormone which can then be reabsorbed (enterohepatic recirculation). There are clinical reports that support the view that enterohepatic recirculation of estrogens decreases in women taking antibiotics such as ampicillin, tetracycline, etc. Conjugated forms of the present estrogenic substances are hardly excreted in the bile, meaning that they are substantially insensitive to drugs that do influence the enterohepatic recirculation of other estrogens.

The above observations serve to explain why the estrogenic substances of the invention can advantageously be used in a method of increasing libido in women. The present estrogenic substances exhibit a surprisingly long in vivo half-life in combination with a relatively high affinitiy for the ERα receptor which is believed to play a crucial role in sexual behaviour. In addition, the present estrogenic substances hardly suffer from drug-drug interactions and thus produce a very consistent, i.e. predictable, impact. Thus, the efficacy of the estrogenic substances of the invention is highly reliable.

DETAILED DESCRIPTION OF THE INVENTION

Accordingly, the present invention is specifically concerned with a method of increasing libido in a woman which comprises administering to said woman an effective amount of an estrogenic component selected from the group consisting of:

substances represented by the following formula

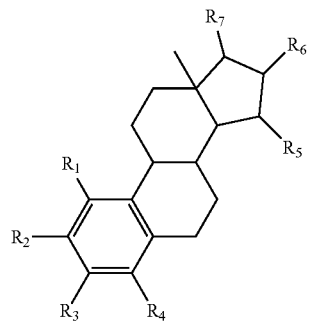

in which formula $R_1, R_2, R_3, R_4$ independently are a hydrogen atom, a hydroxyl group or an alkoxy group with 1-5 carbon atoms; each of $R_5, R_6, R_7$ is a hydroxyl group; no more than 3 of $R_1, R_2, R_3, R_4$ are hydrogen atoms;

precursors capable of liberating a substance according to the aforementioned formula when used in the present method; and mixtures of one or more of the aforementioned substances and/or precursors.

The term "estrogenic component" as used throughout this document encompass substances that are capable of triggering an estrogenic response in vivo, as well as precursors that are capable of liberating such an estrogenic component in vivo when used in accordance with the present invention. In order for estrogenic components to trigger such a response they normally have to bind to an estrogen receptor, which receptors are found in various tissues within the mammalian body.

It is noted that the present invention not only encompasses the use of estrogenic components specifically mentioned in this application, but also metabolites of these hormones that display comparable in vivo functionality. In this context it is observed that, for instance, estriol is a metabolite of 17beta-estradiol. The term "estrogenic substances" as used in this document does not encompass tritium ($^3$H) labeled estrogenic substances such as tritium labeled estetrol.

The present estrogenic substances are distinct from both the biogenic and synthetic estrogens that are commonly applied in pharmaceutical formulations in that they contain at least 4 hydroxyl groups. The present substances are special in that the 5 membered ring in the steroid skeleton comprises 3 hydroxyl substituents rather than 0-2.

Known estrogens that contain at least 4-hydroxyl groups and derivatives thereof are:
1,3,5(10)-estratrien-2,3,15α,16α,17β-pentol 2-methyl ether
1,3,5(10)-estratrien-2,3,15β,16α,17β-pentol 2-methyl ether
1,3,5(10)-estratrien-2,3,16α,17β-tetrol
1,3,5(10)-estratrien-3,4,16α,17β-tetrol 4-methyl ether
1,3,5(10)-estratrien-3,15α,16α,17β-tetrol
1,3,5(10)-estratrien-3,15α,16α,17β-tetrol tetra acetate
1,3,5(10)-estratrien-3,15β,16β,17β-tetrol tetra acetate Preferably, the estrogenic substance applied as the active component in the present composition is a so called biogenic estrogen, i.e. an estrogen that occurs naturally in the human body, a precursor of a biogenic estrogen or mixtures thereof. Because biogenic estrogens are naturally present in the fetal and female body, side-effects are not expected to occur, particularly not if the serum levels resulting from the exogenous administration of such estrogens do not substantially exceed naturally occurring concentrations. Since estetrol serum levels in the fetus are several times higher than those found in pregnant females and knowing that the fetus is particularly vulnerable, estetrol is deemed to be a particularly safe biogenic estrogen. Side-effects are not expected to occur, particularly not if the serum levels resulting from the exogenous administration of such estrogens do not substantially exceed naturally occurring (fetal) concentrations. With synthetic estrogens such as ethinyl estradiol there is a (dose dependent) risk of undesirable side-effects, such as thromboembolism, fluid retention, nausea, bloating, cholelithiasis, headache, breast pain and an enhanced risk of breast cancer with longer term usage.

In a preferred embodiment of the present invention the estrogenic substance contains 4 hydroxyl groups. Also, in the aforementioned formula, $R_1$ preferably represents a hydrogen atom. In said formula preferably at least 2, more preferably at least 3 of the groups $R_1$, $R_2$, $R_3$ and $R_4$ represent a hydrogen atom.

The estrogenic substances according to the formula encompass various enantiomers since the carbon atoms that carry hydroxyl-substituents $R_5$, $R_6$ and $R_7$ are chirally active. In one preferred embodiment, the present estrogenic substance is 15α-hydroxy substituted. In another preferred embodiment the substance is 16α-hydroxy substituted. In yet another preferred embodiment, the substances is 17β-hydroxy substituted. Most preferably the estrogenic substances are 15α,16α,17β-trihydroxy substituted.

In another preferred embodiment of the present invention $R_3$ represents a hydroxyl group or an alkoxy group. In another preferred embodiment the groups $R_1$, $R_2$ and $R_4$ represent hydrogen atoms, in which case, if $R_3$, $R_5$, $R_6$ and $R_7$ are hydroxyl groups, the substance is 1,3,5(10)-estratrien-3,15,16,17-tetrol. A preferred isomer of the latter substance is 1,3,5(10)-estratrien-3,15α,16α,17β-tetrol (estetrol).

The invention also encompasses the use of precursors of the estrogenic substances that constitute the active component in the present method. These precursors are capable of liberating the aforementioned estrogenic substances when used in the present method, e.g. as a result of metabolic conversion. These precursors are preferably selected from the group of androgenic precursors as well as derivatives of the present estrogenic substances. Suitable examples of androgenic precursors include androgens that can be converted into the present estrogenic substances through in vivo aromatisation. Examples of derivatives of the present estrogenic substances that can suitably be used as precursors include such substances wherein the hydrogen atom of at least one of the hydroxyl groups has been substituted by an acyl radical of a hydrocarbon carboxylic, sulfonic acid or sulfamic acid of 1-25 carbon atoms; tetrahydrofuranyl; tetrahydropyranyl; or a straight or branched chain glycosidic residue containing 1-20 glycosidic units per residue.

Typical examples of precursors which can suitably be used in accordance with the invention are esters that can be obtained by reacting the hydroxyl groups of the estrogenic substances with substances that contain one or more carboxy ($M^{+-}OOC-$) groups, wherein $M^+$ represents a hydrogen or (akali)metal cation. Hence, in a particularly preferred embodiment, the precursors are derivatives of the estrogenic substances, wherein the hydrogen atom of at least one of the hydroxyl groups in said formula has been substituted by —CO—R, wherein R is a hydrocarbon radical comprising from 1-25 carbon atoms. Preferably R is hydrogen, or an alkyl, alkenyl or aryl radical comprising from 1-20 carbon atoms.

The present method encompasses protocols wherein the estrogenic component is administered at predetermined, regular intervals as well as a protocol wherein the estrogenic component is administered on demand at the moment a woman wishes to increase her libido.

The term "libido" has been defined above as the urge to engage in sexual activity and intercourse. It is noted that such an urge may be affected by both psychological and fysiological factors (e.g. vaginal atrophy and dyspareunia). In a particularly preferred embodiment of the invention the present method is employed to increase the libido of a female who does not suffer from decreased libido as a result of vaginal atrophy and/or dyspareunia.

The present method may suitably employ enteral or parenteral administration of the estrogenic component. The term "parenteral administration" as used in here encompasses transdermal, intranasal, intravaginal, pulmonary, buccal, subcutaneous, intramuscular and intra-uterine administration. The term "enteral administration" includes oral as well as rectal administration.

Preferably the mode of administration is selected from the group consisting of oral, transdermal, intranasal, intravaginal, pulmonary, rectal, buccal, subcutaneous, intramuscular or intra-uterine administration. More preferably the mode of administration is selected from the group consisting of oral, transdermal, subcutaneous, intramuscular, intranasal, pulmonary and vaginal administration. In a particularly preferred embodiment the present method employs oral, intranasal, intravaginal or rectal administration. Even more preferably the present method employs oral or intranasal administration.

Oral, intranasal, rectal, buccal and pulmonary administration are ideally suited for (at least) once daily administration. Transdermal administration is advantageously applied at frequencies between once a day and once a month. Intravaginal and intrauterine administrations are advantageously operated at administration frequencies between once weekly and once monthly. Subcutaneous and intramuscular administration are suitably done in the form of depot injections at intervals of 1 week to 6 months, preferably at intervals of 4 weeks to 3 months.

For reasons of convenience and also to achieve high compliance rates, the present method preferably utilises administration intervals of 1 day, 1 week or 1 month. Regimens that employ once daily oral or intranasal administration, once weekly transdermal or once monthly intravaginal or subcutaneous administration are particularly preferred.

Irrespective of the mode of administration, the estrogenic component is preferably administered in an amount effective to achieve a blood serum concentration of at least 1 nanogram per liter, more preferably of at least 10 nanogram per liter, most preferably at least 100 nanogram per liter. Generally the resulting blood serum concentration of the estrogenic component will not exceed 100 μg per liter, preferably it will not exceed 50 μg per liter, more preferably it will not exceed 25 μg per liter.

In accordance with the present method the estrogenic component is usually administered in an amount of less than 1 mg per kg of bodyweight per day preferably of less than 0.4 mg per kg of bodyweight per day. In order to achieve a significant impact from the administration of the estrogenic component, it is advisable to administer in an amount of at least 1 μg per kg of bodyweight per day. Preferably, the administered amount is at least 5 μg per kg of bodyweight per day.

Oral administration of the active component is preferably done in an amount of less than 400 μg per kg of bodyweight per day, preferably of less than 200 μg per kg of bodyweight per day. In order to achieve a significant impact from the administration of the active component, it is advisable to orally administer in an amount of at least 2 μg per kg of bodyweight per day. Preferably, the orally administered amount is at least 5 μg per kg of bodyweight per day.

The present method comprises administering to a woman in need of enhanced libido an effective amount of the present estrogenic component. The amounts needed to be effective will differ from individual to individual and are determined by factors such as the individual's endogenous estrogen levels, body weight, route of administration and the efficacy of the particular estrogen substance used. Suitably, in the present method, the estrogenic component is administered in an dosage of at least 0.05 mg per day, preferably of at least 0.1 mg per day. The maximum dosage normally does not exceed 40 mg per day, preferably it does no exceed 20 mg per day.

The present method is particularly suited for increasing libido in hypoestrogenic women. A typical example of hypoestrogenic women are menopausal and postmenopausal females. It is noted that many menopausal and postmenopausal women undergo estrogen replacement therapy, which usually involves the combined administration of an estrogen (often 17-β estradiol) and a progestogen. Since 17-β estradiol is deemed to be less effective in restoring libido than the present estrogenic substances, it is deemed advantageous to administer these estrogenic substances, in addition to or instead of 17-β estradiol, to improve the libido of menopausal or postmenopausal women who are using estrogen replacement therapy.

In a particularly preferred embodiment of the invention the method employs oral administration of the active estrogenic component. The term oral administration as used in here also encompasses oral gavage administration. The inventors have surprisingly found that, despite its low potency, estetrol and related estrogenic substances may advantageously be administered orally. Although the inventors do not wish to be bound by theory, it is believed that the unexpected efficacy of orally administered estetrol-like substances results from the combination of special pharmacokinetic and pharmacodynamic properties of these substances.

The inventors have discovered that the oral bioavailability of estetrol-like substances is surprisingly high and that their in vivo half-life is considerably longer than that of biogenic estrogens. Thus, even though estetrol and estetrol-like substances have relatively low estrogenic potency, they may effectively be administered orally.

Another important advantage of oral administration of estetrol and estetrol-like substances resides in the fact that the hepatic effects of these substances are deemed to be minimal since they are hardly metabolised during the so called "first pass". The first-pass effect of drugs given orally refers to the process of drug degradation by the liver during a drug's transition from initial ingestion to circulation in the blood stream. After resorption from the intestinal lumen, orally applied active ingredients enter the organism via the liver. This fact is of specific importance for estrogenic agents as the liver is a target organ for estrogens; oral intake of estrogens results in strong estrogenic effects in the liver. Therapeutically equivalent doses of biogenic estrogens, when applied orally, result in clear responses of hepatic parameters, such as increase of SHBG, CBG, angiotensinogen and HDL (high density lipoprotein). These hepatic effects of estrogens are also observed when equine estrogen formulations (so-called conjugated estrogens) are used. Ethinyl estradiol and diethylstilbestrol (DES) have an even greater hepatic estrogenicity. Elger et al., J. Steroid Biochem. Molec., Biol. (1995), 55(3/4), 395-403, have reported that EE or DES have much higher hepato-cellular than systemic estrogenicity: in relation to FSH-secretion inhibitory activity these estrogens are 4-18 times more active in the liver than estrone sulfate.

Regular administration of estrogens during prolonged periods of time has been associated with endometrial proliferation in women. It is widely accepted that "unopposed" estrogen therapy substantially increases the risk of endometrial cancer (Cushing et al., 1998. Obstet. Gynecol.91, 35-39; Tavani et al., 1999. Drugs Aging, 14, 347-357). In addition, there is also evidence of a significant increase in breast cancer with long-term (10-15 years) use of estrogen therapy (Tavani et al., 1999. Drugs Aging, 14, 347-357; Pike et al., 2000. Steroids, 65, 659-664).

In order to counteract any potential negative effects of unopposed estrogen administration, particularly in case of frequent administration (e.g. on average more than 2, particularly more than 3 times a week) it is preferred to co-administer a progestogenic component to inhibit estrogen stimulation of the endometrium (Beral et al., 1999. J. Epidemiol. Biostat., 4, 191-210) or to administer a progestogenic component at least during a period of ten day at least every three months.

Examples of progestogenic components which may suitably be used in accordance with the present invention include: progesterone, levonorgestrel, norgestimate, norethisterone, dydrogesterone, drospirenone, 3-beta-hydroxydesogestrel, 3-keto desogestrel (=etonogestrel), 17-deacetyl norgestimate, 19-norprogesterone, acetoxypregnenolone, allylestrenol, anagestone, chlormadinone, cyproterone, demegestone, desogestrel, dienogest, dihydrogesterone, dimethisterone, ethisterone, ethynodiol diacetate, flurogestone acetate, gastrinon, gestodene, gestrinone, hydroxymethylprogesterone, hydroxyprogesterone, lynestrenol (=lynoestrenol), medrogestone, medroxyprogesterone, megestrol, melengestrol, nomegestrol, norethindrone (=norethisterone), norethynodrel, norgestrel (includes d-norgestrel and dl-norgestrel), norgestrienone, normethisterone, progesterone, quingestanol, (17alpha)-17-hydroxy-11-methylene-19-norpregna-4,15-diene-20-yn-3-one, tibolone, trimegestone, algestone acetophenide, nestorone, promegestone, 17-hydroxyprogesterone esters, 19-nor-17hydroxyprogesterone, 17alpha-ethinyl-estosterone, 17alpha-ethinyl-19-nor-testosterone, d-17beta-acetoxy-13beta-ethyl-17alpha-ethinyl-gon-4-en-3-one oxime and precursors of these compounds that are capable of liberating these progestogens in vivo when used in the present method. Preferably the progestogen used in the present method is selected from the group consisting of progesterone, desogestrel, etonogestrel, gestodene, dienogest, levonorgestrel, norgestimate, norethisterone, drospirenone, trimegestone, dydrogesterone, precursors of these progestogens and mixtures thereof.

The progestogenic component is suitably administered in an amount which is equivalent to an oral dosage of 30-750 μg levonorgestrel, more preferably of 50-400 μg levonorgestrel.

In another preferred embodiment of the invention the present method employs the co-administration of the estrogenic component with an androgenic component. It was found that in some cases the combined administration of an estrogenic and an androgenic component is more effective than the administration of the estrogenic component per se in achieving improved libido. The androgenic component may suitably be selected from the group consisting of dehydroepiandrosterone (DHEA); DHEA-sulphate; testosterone; testosterone esters such as testosterone undecanoate, testosterone propionate, testosterone phenylpropionate, testosterone isohexanoate, testosterone enantate, testosterone bucanate, testosterone decanoate, testosterone buciclate; danazol; gestrinone; methyltestosterone; mesterolon; stanozolol; androstenedione; dihydrotestosterone; androstanediol; metenolon; fluoxymesterone; oxymesterone; methandrostenolol; MENT; precursors capable of liberating these androgens when used in the present method and mixtures thereof. More preferably the androgenic component is selected from the group consisting of DHEA, testosterone esters, androstenedione, precursors capable of liberating these androgens when used in the present method and mixtures thereof. Most preferably the androgenic component is selected from the group consisting of dehydroepiandrosterone, esters of testosterone and mixtures thereof.

Preferably the testosterone esters employed in the present method comprise an acyl group which comprises at least 6, more preferably from 8-20 and preferably 9-13 carbon atoms. Most preferably the androgens used in the present method are DHEA and/or testosterone undecanoate. These androgens offer the advantage that they can effectively be used in oral dosage units.

It is noted that, for instance, DHEA, testosterone undecanoate and androstenedione are precursors of testosterone and that said precursors per se exhibit virtually no affinity for androgen receptors in the female body. The effectiveness of the androgens within the method of the invention is determined by their functionally active form, which may well be different from the form in which they are administered.

In the present method the androgen is preferably provided in an amount equivalent to an oral dosage of at least 5 mg DHEA, which is equivalent to an oral dosage of at least 1 mg testosterone undecanoate. More preferably the androgen is provided in an amount which is equivalent to an oral dosage of a least 10 mg DBEA, most preferably of at least 20 mg DHEA. Usually the androgen dosage employed will not exceed the equivalent of an oral dosage of 250 mg DHEA, which is equivalent to an oral dosage of 50 mg testosterone undecanoate. Preferably the androgen is administered in a dosage which does not exceed the equivalent of an oral dosage of 120 mg DHEA, more preferably it does not exceed the equivalent of an oral dosage 60 mg DHEA.

The present invention is further illustrated by the following examples, which, however, are not to be construed as limiting. The features disclosed in the foregoing description, in the following examples and in the claims may, both separately and in any combination thereof, be material for realising the invention in diverse forms thereof

EXAMPLES

Example 1

Vaginal cornification was chosen as a tissue-specific and estrogen-sensitive endpoint to determine the estrogenicity of estetrol (E4), after both oral and subcutaneous administration, in hypoestrogenic rats. 17α-ethinylestradiol (EE), 17β-estradiol (E2) and vehicle (10% ethanol/sesame oil) served as controls in these bioassays.

Uterine weight increase in the rat is more commonly used as a measure of estrogenicity. However, uterine weight also responds to progesterone, testosterone, and other agents not characteristically regarded as estrogens. In the early 1920s it was discovered that follicular fluid from the pig ovary contained a factor(s) that caused cornification/keratinization of the vaginal epithelium in the rat (Allen and Doisy, 1923, JAMA, 81,819-821; Allen and Doisy, 1924, Am. J. Physiol., 69, 577-588). The so-called vaginal cornification response in rats subsequently provided a bioassay for testing estrogenicity. Vaginal epithelial cornification/keratinization in ovariectomized rats can be produced only by compounds considered to be true estrogens (Jones et al, 1973, Fert. Steril. 24, 284-291). Vaginal epithelial cornification/keratinization represents, therefore, a highly selective endpoint to determine the potency of estrogens (Reel et al., 1996, Fund. Appli. Toxicol. 34, 288-305).

Adult intact female CD rats were ovariectomized to induce estrogen deficiency. Vaginal lavages were performed daily for seven days to ensure that the rats demonstrated castrate vaginal smears (predominance of leukocytes in the vaginal smear, and similar in appearance to a diestrous vaginal smear). Castrate vaginal smears are indicative that complete ovanectomy was achieved. Treatment commenced following completion of the 7 days of smearing (day 0=first day of dosing). Animals were dosed, once daily for 7 consecutive days. Daily vaginal lavages continued to be obtained for 7 days after dosing was initiated in order to detect vaginal cornification, as an indication of an estrogenic response. A drop of vaginal washings was placed on a glass slide and examined by light microscopy to detect the presence or absence of cornified epithelial cells. Vaginal lavages were obtained prior to dosing on days 0-6 and prior to necropsy on day 7.

The vaginal cornification bioassay was performed in order to determine the estrogenic profile of E4 when given subcutaneously (sc) to ovariectomized adult rats. E2 was used as a positive control. The vehicle (10% ethanol/sesame oil) served as the negative control. Steroids were dissolved in absolute ethanol and then brought to the final concentration with sesame oil (10% ethanol in sesame oil). A vaginal estrogenic response occurred in 8/8 rats by day 2 and persisted through day 7 in rats injected sc with 50 µg/kg/day E2 for 7 days (Table 1). Animals treated with the vehicle did not exhibit vaginal epithelial cornification (Table 1). The onset of vaginal epithelial cornification was dose-dependent in rats injected sc with 0.1, 0.3, 1.0, and 3.0 mg/kg/day E4 and started at the same day of treatment (Day 2) as observed for E2 (Table 1). At 0.1 mg/kg/day E4 already 4/8 rats and at 0.3 mg/kg/day E4 even 7/8 rats exhibited a vaginal estrogenic response by day 7. At 1.0 and 3.0 mg/kg/day E4 all rats showed a vaginal estrogenic response by day 7 (Table 1).

TABLE 1

Vaginal estrogenic response in ovariectomized rats treated subcutaneously (sc) with 17β-estradiol (E2) or estetrol (E4). Data are expressed as the number of rats showing vaginal cornification over the number of rats (ratio) treated.

| Treatment Group | Dosing route | Number of Rats Exhibiting Estrogenic Response/ Number of Rats Treated Day of Study | | | | | | | |
|---|---|---|---|---|---|---|---|---|---|
| | | Day 0 | Day 1 | Day 2 | Day 3 | Day 4 | Day 5 | Day 6 | Day 7 |
| 0.05 mg/kg/day E2 | sc | 0/8 | 0/8 | 8/8 | 8/8 | 8/8 | 8/8 | 8/8 | 8/8 |
| Vehicle Control | sc | 0/8 | 0/8 | 0/8 | 0/8 | 0/8 | 0/8 | 0/8 | 0/8 |

TABLE 1-continued

Vaginal estrogenic response in ovariectomized rats treated subcutaneously (sc) with 17β-estradiol (E2) or estetrol (E4). Data are expressed as the number of rats showing vaginal cornification over the number of rats (ratio) treated.

| Treatment Group | Dosing route | Number of Rats Exhibiting Estrogenic Response/ Number of Rats Treated Day of Study | | | | | | | |
|---|---|---|---|---|---|---|---|---|---|
| | | Day 0 | Day 1 | Day 2 | Day 3 | Day 4 | Day 5 | Day 6 | Day 7 |
| 0.1 mg/kg/day E4 | sc | 0/8 | 0/8 | 0/8 | 1/8 | 1/8 | 4/8 | 3/8 | 4/8 |
| 0.3 mg/kg/day E4 | sc | 0/8 | 0/8 | 1/8 | 5/8 | 7/8 | 6/8 | 7/8 | 7/8 |
| 1.0 mg/kg/day E4 | sc | 0/8 | 0/8 | 1/8 | 6/8 | 8/8 | 7/8 | 8/8 | 8/8 |
| 3.0 mg/kg/day E4 | sc | 0/8 | 0/8 | 3/8 | 8/8 | 8/8 | 8/8 | 8/8 | 8/8 |

The vaginal cornification bioassay was performed in order to determine the estrogenic profile of E4 when given orally (po) to ovariectomized adult rats. EE was used as a positive control. The vehicle (10% ethanol/sesamne oil) served as the negative control. Steroids were dissolved in absolute ethanol and then brought to the final concentration with sesame oil (10% ethanol in sesame oil). A vaginal estrogenic response occurred in all rats (8/8) given 50 µg/kg/day EE po by day 7 (Table 2). Similarly, vaginal epithelial cornification was observed in all rats (8/8) treated po with either 0.1, 0.3, 1.0, or 3.0 mg/kg/day E4 by day 7 (Table 2whereas animals treated with the vehicle did not exhibit vaginal epithelial cornification (0/8). Surprisingly, even in rats given relatively low doses of E4 (e.g. 0.1 mg/kg/day), the onset of vaginal cornification (defined as the amount of animals responding at days 1-3 of the study) was faster in po-treated (Table 2)than in sc-treated animals (Table 1)), demonstrating estetrol's superb bioavailability characteristics after oral administration life, single dose studies were performed in female Sprague Dawley rats followed by frequent blood sampling over a 24 hours interval.

Female Sprague Dawley rats were equipped with a permanent silatic heart catheter, as described by Kuipers et al. (1985, Gastroenterology, 88, 403-411). Rats were allowed to recover from surgery for 5 days and were than administered 0.05, 0.5, or 5 mg/kg E4 in 0.5 ml arachis oil. For sc administration, E4 was injected in the neck area using a 1 ml syringe and 20 g needle. For po administration of E4, rats were lightly anaesthesized with halothene/$N_2O/O_2$ and E4 was directly applied intragastrically using a plastic stomach intubator. Blood samples were subsequently collected via the heart catheter in heparinized tubes at 0.5, 1, 2, 4, 8 and 24 hours. Erytlrocytes were removed by centrifugation at 5000×g for 10 minutes at 4° C. and blood plasma was stored at −20° C. After thawing the plasma samples, liquid-liquid extraction (hexane/diethylether) was employed to prepare the E4-con-

TABLE 2

Vaginal estrogenic response in ovariectomized rats treated orally (po) with 17α-ethinyl estradiol (EE) or estetrol (E4). Data are expressed as the number of rats showing vaginal cornification over the number of rats (ratio) treated.

| Treatment Group | Dosing route | Number of Rats Exhibiting Estrogenic Response/ Number of Rats Treated Day of study | | | | | | | |
|---|---|---|---|---|---|---|---|---|---|
| | | Day 0 | Day 1 | Day 2 | Day 3 | Day 4 | Day 5 | Day 6 | Day 7 |
| 0.05 mg/kg/day EE | po | 0/8 | 1/8 | 3/8 | 8/8 | 8/8 | 8/8 | 8/8 | 8/8 |
| Vehicle Control (2 ml/kg/day) | po | 0/8 | 0/8 | 0/8 | 0/8 | 0/8 | 0/8 | 0/8 | 0/8 |
| 0.1 mg/kg/day E4 | po | 0/8 | 0/8 | 1/8 | 7/8 | 8/8 | 8/8 | 8/8 | 8/8 |
| 0.3 mg/kg/day E4 | po | 0/8 | 0/8 | 1/8 | 7/8 | 8/8 | 8/8 | 8/8 | 8/8 |
| 1.0 mg/kg/day E4 | po | 0/8 | 0/8 | 4/8 | 8/8 | 8/8 | 8/8 | 8/8 | 8/8 |
| 3.0 mg/kg/day E4 | po | 0/8 | 0/8 | 6/8 | 8/8 | 8/8 | 8/8 | 8/8 | 8/8 |

Example 2

To evaluate the oral (po) and subcutaneous (sc) bioavailability of estetrol (E4) and to determine the elimination halftaining plasma samples for HPLC analysis (Perkin Elmer 200) and tandem mass spectrometry using a PE Sciex 3000 tandem mass spectrometer and APCI interface. With each sample batch, a calibration curve with 6 calibrators was recorded. The calibration curve was calculated using linear regression (correlation coefficient>0.98), which permitted quantitation of plasma concentrations. For each rat plasma, sampled at different time intervals, data were collected.

Plasma E4 concentration data were analysed with "WinNonLin, edition 3.1" and involved pharmacokinetic parameters for $C_{max}$, half-life and $AUC_{0-24}$. Especially, using the lower and intermediate dose levels of 0.05, 0.5 mg/kg, E4 demonstrated an oral bioavailability equal to the bioavailability obtained with sc administration (80-100%). At the highest dose level tested, 5.0 mg/kg E4, absorption kinetics gave rise to an oral bioavailability approximating 30-60% of sc administered E4. Interestingly, E4 demonstrated a relatively long half-life of 2-3 hours, enabling the detection of bioactive levels of unconjugated E4 at all time points over a 24 hour interval in the sc and po dosing experiments.

Example 3

Established competitive steroid binding assays were used to determine the relative binding affinity of estetrol (E4), as compared to 17α-ethinylestradiol(EE) and 17β-estradiol (E2), to human Estrogen Receptor (ER) α- and β-forms.

The method employed was adapted from the scientific literature and described in detail by Osbourn et al. (1993, Biochemistry, 32, 6229-6236). Recombinant human ERα and ERβ proteins were purified from transfected Sf9-cells. The in vitro assays involved the use of either ERα or ERβ proteins and [$^3$H]E2, at a fixed concentration of 0.5 nM, as the labeled ligand. Recombinant human ERα or ERβ proteins were dissolved in binding buffer (10 mM Tris-HCL, pH 7.5, 10% glycerol, 1 mM DTT, 1 mg/ml BSA) and duplicate aliquots were then incubated with [$^3$H]E2 at a final concentration of 0.5 nM, together with a vehicle control (0.4% DMSO), or the same amount of vehicle containing increasing concentrations of unlabeled steroid ligands as competitors. After incubation for 2 h at 25° C., the unbound ligands were removed and the amounts of [$^3$H]E2 bound to either ERα or ERβ proteins were measured. The average amounts of [$^3$H]E2 bound to either ERα or ERβ proteins at each concentration of competitor were used to make inhibition curves. IC50 values were subsequently determined by a non-linear, least squares regression analysis. Inhibition constants (Ki) were calculated using the equation of Cheng and Prusoff (Cheng et al., 1973, Biochem. Pharmacol., 22, 3099-3108), using the measured IC50 of the tested compounds, the concentration of radioligand employed in the assay, and the historical values for the Kd of the radioligand, which were established as 0.2 nM and 0.13 nM for ERα and ERβ, respectively.

Biochemical assay results for E4 are presented as the percent inhibition of specific binding in three separate experiments (Table 3). For comparision of binding affinities of E4, EE and E2 to human ERα and ERβ proteins, experimentally observed Ki values are shown in Table 4. As compared to EE and E2, E4 demonstrates a unique binding profile with a strong preference (400%) for binding to the ERα protein (Table 4). In contrast, Ki values for ERβ protein are more pronounced for EE and E2 steroid ligands (Table 4).

TABLE 3

Percent inhibition of specific binding to ERα and ERβ proteins using E4 as unlabeled steroid ligand and 0.5 nM [3H] as labeled competitor. Results of three separate experiments are shown.

| E4 final concentration | Percent inhibition of specific binding in | | | | | |
| --- | --- | --- | --- | --- | --- | --- |
| | ERα steroid binding assay | | | ERβ steroid binding assay | | |
| | Test 1 | Test 2 | Test 3 | Test 1 | Test 2 | Test 3 |
| 1 μM | 98 | nd | nd | 87 | 90 | 95 |
| 0.3 μM | 92 | 94 | 101 | 74 | 74 | 77 |
| 0.1 μM | 83 | 85 | 86 | 56 | 54 | 50 |
| 0.03 μM | 64 | 66 | 63 | 19 | 25 | 30 |
| 10 nM | 43 | 32 | 28 | nd | nd | nd |
| 3 nM | 26 | 17 | 11 | nd | nd | nd | nd: not determined

Table 4: Experimentally determined inhibition constants (Ki) for estetrol (E4), 17α-ethinylestradiol (EE) and 17β-estradiol (E2), to human ERα and ERβ proteins. Relative preference for binding to ERα protein is also shown.

| Steroid ligands | Ki ERα (nM) | Ki ERβ (nM) | Relative ERα/ERβ preference(%) |
| --- | --- | --- | --- |
| EE | 0.23 | 0.025 | 11 |
| E2 | 0.21 | 0.015 | 7 |
| E4 | 4.9 | 19 | 400 |

Example 4

An established competitive steroid-binding assay (Hammond and Lahteenmaid. 1983. Clin Chem Acta 132:101-110) was used to determine the relative binding affinity of estetrol (E4), 17α-ethinylestradiol(EE2), 17β-estradiol (E2), testosterone (T) and 5α-dihydrotestosterone (DHT) for human sex Hormone Binding Globulin (SHBG).

Human SHBG was purified from transgenic mouse serum, as described previously (Avvakumov G V et al., 2000. J Biol Chem 275: 25920-25925). The human SHBG prepared in this way was assessed to be >99% pure by polyacrylamide gel electrophoresis under denaturing conditions. Its steroid-binding characteristics are indistinguishable from SHBG in human serum (Avvakumov G V et al., 2000. J Biol Chem 275: 25920-25925). The in vitro assay involved the use of the purified human SHBG and [$^3$H]DHT or [$^3$H]estradiol as labeled ligands. Human SHBG was treated for 30 min at room temperature with a dextran-coated charcoal (DCC) suspension in phosphate buffered saline (PBS) to remove any steroid ligand. After centrifugation (2,000×g for 10 min) to sediment the DCC, the supernatant containing the human SHBG was diluted in PBS to a concentration of 1 nM based on its steroid binding capacity.

Duplicate aliquots (100 μl) of this human SHBG solution were then incubated with an equal volume of either [$^3$H]DHT or [$^3$H]estradiol at 10 nM, together with 100 μl of PBS alone or the same amount of PBS containing increasing concentrations of unlabeled steroid ligands as competitors in polystyrene test tubes. After incubation for 1 h at room temperature the reaction mixtures were placed in an ice bath for a further 15 min. Aliquots (600 μl) of an ice cold suspension of DCC were then added to each tube, and after a brief 2 seconds mixing, each tube was incubated in an ice bath for either 10 min or 5 min depending on whether [³H]DHT or [³H]estradiol were being used as labeled ligands, respectively. The unbound ligands adsorbed to DCC were then removed by centrifugation (2,000×g for 15 min at 4 C), and the amounts of [³H]labeled ligands bound to SHBG were counted in 2 ml ACS scintillation cocktail using in liquid scintillation spectrophotometer. The average amounts of [³H]labeled ligands bound to SHBG at each concentration of competitor (B) were expressed as a percentage of the average amounts of [³H] labeled ligands bound to SHBG in the absence of competitor ($B_0$), and were plotted against the concentration of competitor in each assay tube.

As is clearly apparent from these competitive binding assays, estetrol does not bind at all to human SHBG when tested with either [³H]DHT or [³H]estradiol as labeled ligands. This is in marked contrast with reference steroids ethinylestradiol, 17β-estradiol, testosterone and 5α-dihydrotestosterone, which, in this order, show an increased relative binding affinity for human SHBG. Importantly, estetrol binding to SHBG was negligible when compared with the other estrogens tested, ethinylestradiol and 17β-estradiol.

Example 5

Dosage Units for Oral Administrations

The present estrogenic components may suitably be processed, together with additives, excipients and/or flavoring agents customary in galenic pharmacy, in accordance with the conventional methods into the usual forms of administration. For oral administration, suitable are, in particular, tablets, dragees, capsules, pills, suspensions, or solutions.

Estetrol tablets: 1,000 tablets of 185 mg, containing 1.5 mg estetrol, are produced from the following formulation:

| | |
|---|---|
| Estetrol | 1.500 g |
| Polyvinylpyrrolidone (Kollidon 25 ® ex BASF) | 13.500 g |
| Lactose | 135.795 g |
| Microcrystalline cellulose (Avicel PH 101 ®) | 26.250 g |
| Glyceryl palmitostearate (Precirol ®) | 2.775 g |
| Anhydrous colloidal silica (Aerosil 200 ®) | 1.000 g |
| Crospovidone (Polyplasdone XL ®) | 4.000 g |
| Coloring agent | 0.180 g |

Example 6

Drug Delivery System for Intranasal Administration

Suitable nontoxic pharmaceutically acceptable carriers for use in a drug delivery system for intranasal administration of the present estogenic component will be apparent to those skilled in the art of nasal pharmaceutical formulations. For those not skilled in the art, reference is made to "Remington's Pharmaceutical Sciences", 4th edition, 1970. Obviously, the choice of suitable carriers will depend on the exact nature of the particular nasal dosage form desired, e.g. whether the estrogenic component is to be formulated into a nasal solution (for use as drops or as a spray), nasal microspheres, a nasal suspension, a nasal ointment or a nasal gel, as well as on the identity of the estrogenic component.

Examples of the preparation of typical nasal compositions are set forth below.

Nasal Solution:
  5 mg of estetrol is combined with 10 mg of Tween 80. That mixture is then combined with a quantity of isotonic saline sufficient to bring the total volume to 50 ml. The solution is sterilised by being passed through a 0.2 micron Millipore filter.

Nasal Gel:
  250 ml of isotonic saline are heated to 80° C. and 1.5 g of Methocel are added, with stirring. The resultant mixture is allowed to stand at room temperature for 2 hours. Then, 10 mg of estetrol are mixed together with 10 mg of Tween 80. The estetrol/Tween mixture and a quantity of isotonic saline sufficient to bring the total volume to 500 ml were added to the gel and thoroughly mixed.

Example 7

A clinical study is conducted in 40 postmenopausal women who are not using hormone replacement therapy and who do not suffer from vaginal atrophy or dyspareunia. In a baseline cycle, coitus frequency and sexual satisfaction (female orgasm) are recorded.

Each participant receives blinded medication in 2 differently labeled bottles, filled with tablets. One bottle comprises tablets that contain 2 mg estetrol, whilst the other bottle contains identical placebo tablets. The participants are allowed to choose from which bottle to take a tablet, but are instructed not to use more than 1 tablet per 24 hours and not more than 2 tablets a week. The total duration of the study is 4 months.

It is found that during the study participants use significantly more estetrol containing tablets than placebo's. In addition, analysis of the data shows that women who mainly used estetrol containing tablets report improved libido and sexual enjoyment in comparison to baseline.

Consequently, it can be concluded that oral administration of 2 mg estetrol leads to an improvement of libido and sexual enjoyment in some of these users, whilst no undesirable side-effects are reported.

The invention claimed is:

1. A method of increasing libido in a woman, comprising administering to said woman an effective amount of an estrogenic component selected from the group consisting of: substances represented by the following formula

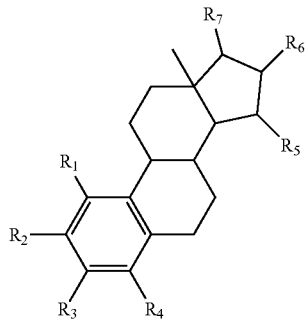

in which formula $R_1$, $R_2$, $R_3$, $R_4$ independently are a hydrogen atom, a hydroxyl group or an alkoxy group with 1-5 carbon atoms; each of $R_5$, $R_6$, $R_7$ is a hydroxyl group; no more than 3 of $R_1$, $R_2$, $R_3$, $R_4$ are hydrogen atoms;
  derivatives of these substances wherein the hydrogen atom of at least one of the hydroxyl groups in said formula has been substituted by an acyl radical of a hydrocarbon carboxylic, sulfonic acid or sulfamic acid of 1-25 carbon atoms; tetrahydrofuranyl; tetrahydropyranal; or a straight or branched chain glycosydic residue containing 1-20 glycosidic units per residue; and mixtures of one or more of the aforementioned substances and/or precursors.

2. The method according to claim 1, wherein $R_3$ represents a hydroxyl group or an alkoxy group.

3. The method according to claim 1, wherein at least 3 of the groups $R_1$, $R_2$, $R_3$, and $R_4$ represent hydrogen atoms.

4. The method according to claim 1, wherein the method comprises oral, transdermal, intranasal, rectal, pulmonary, buccal, subcutaneous, intravaginal or intra-uterine administration of the estrogenic component.

5. The method according to claim 4, wherein the method comprises oral or intranasal administration.

6. The method according to claim 1, wherein the estrogenic component is administered in an amount effective to achieve a blood serum concentration of at least 1 nanogram per liter.

7. The method according to claim 1, wherein the estrogenic component is administered in an amount effective to achieve a blood serum concentration of at least 10 nanograms per liter.

8. The method according to claim 1, wherein the estrogenic component is administered in a dosage of at least 1 µg per kg of bodyweight.

9. The method according to claim 1, wherein the estrogenic component is administered in a dosage of at least 5 µg per kg of bodyweight.

10. The method according to claim 1, wherein the estrogenic component is co-administered with a progestogenic component.

11. The method according to claim 1, wherein the estrogenic component is co-administered with an androgenic component.

12. The method according to claim 1, wherein the estrogenic component is administered orally.

* * * * *